United States Patent
Choi et al.

(10) Patent No.: US 11,033,505 B2
(45) Date of Patent: Jun. 15, 2021

(54) ORAL COMPLEX PREPARATION COMPRISING FAT-SOLUBLE DRUG AND SOLID PREPARATION COATED WITH OIL-PROOF MATERIAL

(71) Applicants: Korea United Pharm, Inc., Sejong (KR); United Science R&D Center, Sejong (KR)

(72) Inventors: Yun Woong Choi, Gyeonggi-do (KR); Dae Chul Ha, Sejong (KR); In Ho Kwon, Sejong (KR); Byung Jin Kim, Sejong (KR); Hee Yong Song, Sejong (KR); Min-Seok Kwon, Sejong (KR); Byung Gu Min, Seoul (KR); Sang Min Cho, Gyeonggi-do (KR); Jae Sang Jang, Incheon (KR)

(73) Assignees: Korea United Pharm, Inc., Sejong (KR); United Science R&D Center, Sejong (KR)

( * ) Notice: Subject to any disclaimer, the term of this patent is extended or adjusted under 35 U.S.C. 154(b) by 0 days.

(21) Appl. No.: 16/075,519

(22) PCT Filed: Feb. 3, 2017

(86) PCT No.: PCT/KR2017/001200
§ 371 (c)(1),
(2) Date: Aug. 3, 2018

(87) PCT Pub. No.: WO2017/135739
PCT Pub. Date: Aug. 10, 2017

(65) Prior Publication Data
US 2019/0083409 A1    Mar. 21, 2019

(30) Foreign Application Priority Data
Feb. 5, 2016    (KR) .................. 10-2016-0015306

(51) Int. Cl.
*A61K 9/48*    (2006.01)
*A61K 9/00*    (2006.01)
(Continued)

(52) U.S. Cl.
CPC .............. *A61K 9/4808* (2013.01); *A61K 9/00* (2013.01); *A61K 9/20* (2013.01); *A61K 9/28* (2013.01);
(Continued)

(58) Field of Classification Search
None
See application file for complete search history.

(56) References Cited

U.S. PATENT DOCUMENTS 5,916,590 A * 6/1999 Cody .................. A61K 9/4866
424/452
6,448,323 B1 * 9/2002 Jordan .................. C08K 5/521
524/451
(Continued)

FOREIGN PATENT DOCUMENTS

EP    1803440 A1 *  7/2007  ............... A61P 3/00
EP    2229939 A1     9/2010
(Continued)

OTHER PUBLICATIONS

Bolourchian, et al., "The Effect of PEG Molecular Weights on Dissolution Behavior of Simvastatin in Solid Dispersions," Iranian Journal of Pharmaceutical Research 12:11-20 (2013).

*Primary Examiner* — Melissa S Mercier
(74) *Attorney, Agent, or Firm* — Cooley LLP

(57) ABSTRACT

The present invention relates to an oral complex preparation comprising: a capsule containing a fat-soluble first drug; and a solid preparation containing a second drug, the solid preparation being embedded into the capsule and including an oil-proof material coating layer on the surface thereof (Continued)

The oral complex preparation of the present invention prepared by embedding the solid preparation including the oil-proof material coating layer on the surface thereof and containing the second drug into the capsule containing the fat-soluble first drug enables two types of drug ingredients to be simultaneously administered. At this time, the oral complex preparation of the present invention can independently transfer each of two types of the active ingredients to a desired region without loss of the active ingredients since the oral complex preparation by enabling the oil-proof material coating layer on the surface of the solid preparation to block elution of the active ingredients of the solid preparation by the fat-soluble first drug or occurrence of side effects with the fat-soluble first drug.

15 Claims, 1 Drawing Sheet

(51) Int. Cl.
| | |
|---|---|
| *A61K 9/50* | (2006.01) |
| *A61K 31/202* | (2006.01) |
| *A61K 31/40* | (2006.01) |
| *A61K 9/20* | (2006.01) |
| *A61K 9/28* | (2006.01) |
| *A61K 31/505* | (2006.01) |
| *A61K 31/232* | (2006.01) |

(52) U.S. Cl.
CPC .............. *A61K 9/48* (2013.01); *A61K 9/4825* (2013.01); *A61K 9/4833* (2013.01); *A61K 9/4858* (2013.01); *A61K 9/4866* (2013.01); *A61K 9/50* (2013.01); *A61K 31/202* (2013.01); *A61K 31/232* (2013.01); *A61K 31/40* (2013.01); *A61K 31/505* (2013.01)

(56) References Cited

U.S. PATENT DOCUMENTS

2013/0115281 A1* 5/2013 Draper ................ A61K 9/5084
424/452
2014/0328908 A1* 11/2014 Kaye ...................... A61K 45/06
424/452

FOREIGN PATENT DOCUMENTS

| | | | | |
|---|---|---|---|---|
| EP | 2517697 A1 | 10/2012 | | |
| JP | 2008-517040 A | 5/2008 | | |
| JP | 2013-527205 A | 6/2013 | | |
| KR | 10-2013-0039797 A | 4/2013 | | |
| KR | 10-2014-0131859 A | 11/2014 | | |
| WO | WO-2005018618 A1 * | 3/2005 | ........... | A61K 9/2866 |
| WO | WO-2005030183 A2 * | 4/2005 | ........... | A61K 9/2054 |
| WO | WO2008-066899 A2 | 6/2008 | | |
| WO | WO2012-032417 A2 | 3/2012 | | |
| WO | WO2013-155430 A1 | 10/2013 | | |
| WO | WO 2013-176455 A1 | 11/2013 | | |
| WO | WO 2016-024844 A1 | 2/2016 | | |

* cited by examiner

ORAL COMPLEX PREPARATION COMPRISING FAT-SOLUBLE DRUG AND SOLID PREPARATION COATED WITH OIL-PROOF MATERIAL

CROSS-REFERENCE TO RELATED APPLICATIONS

This application is a U.S. national phase application of International PCT Patent Application No. PCT/KR2017/001200, which was filed on Feb. 3, 2017, which claims priority to Korean Patent Application No. 10-2016-0015306, filed Feb. 5, 2016. These applications are incorporated herein by reference in their entireties.

TECHNICAL FIELD

The present invention relates to an oral complex preparation comprising: a capsule containing a fat-soluble first drug; and a solid preparation containing a second drug, the solid preparation being embedded into the capsule and including an oil-proof material coating layer on the surface thereof.

BACKGROUND ART

A soft capsule, as a formulation widely used in an oral administration preparation for medication convenience, may be a form in which solid and liquid drugs are filled in an elastic shell such as gelatin. A soft capsule for oral administration is manufactured by heat-sealing the active ingredients after injecting active ingredients, and the sealed part is opened in the stomach or the like to rapidly release the contents.

Meanwhile, studies are underway on a method of producing the soft capsule in the form of a complex preparation, which administers two or more drugs to exhibit complementary and/or synergistic medicinal effects and includes two or more active ingredients all together to facilitate taking medicine. As an example of the soft capsule, there is a complex preparation simultaneously comprising an omega-3 fatty acid ester and an HMG-CoA reductase inhibitor conceived to effectively lower the levels of cholesterol and triglycerides in blood at the same time in a hypercholesterolemic patient requiring adjustment of the level of triglycerides in blood.

That is, the omega-3 fatty acid ester functions to lower serum triglycerides (TG), lower blood pressures and pulse rates of systole and diastole, and lower activities of a blood coagulating factor VII phospholipid complex without causing any side effects. Although a statin-based drug that is the HMG-CoA reductase inhibitor has been known to reduce the risk of coronary heart disease (CHD) to about one third, the statin-based drug has a limited effect on TG and serum high-density lipoprotein (HDL). Therefore, a complex preparation comprising both of these ingredients is useful in the hypercholesterolemic patient requiring adjustment of the level of triglycerides in blood.

For example, an oral complex composition comprising an omega-3 fatty acid ester and an HMG-CoA reductase inhibitor, and a method of preparing the same are described in Korean Patent Laid-Open Publication No. 10-2012-109950 (1). Further, a pharmaceutical complex preparation comprising: an omega-3 fatty acid inner layer; a water-soluble polymer intermediate layer; and an outer layer of the HMG-CoA reductase inhibitor or pharmaceutically acceptable salts thereof is disclosed in Korean Patent Laid-Open Publication No. 10-2013-104059 (2).

However, a statin-based drug is uniformly coated on an outer layer including omega-3 in inventions disclosed in documents (1) and (2). Therefore, the composition and preparation according to the inventions are formulations with a much greater surface area than general tablets, and accordingly may cause deterioration of stability, a decrease in content, and increases in related substances due to interaction with an external environment such as moisture, low pH, or the like, which makes it very difficult to adjust an elution pattern of the statin-based drug, and has a high likelihood of generating a problem in content uniformity.

Accordingly, as a result of conducting research and making efforts to provide an oral complex preparation including a solid preparation containing a second drug, such as a statin-based drug, in a capsule containing a fat-soluble first drug, such as an omega-3 fatty acid or an alkyl ester thereof, the present inventors have solved the problems of existing complex preparations, and have completed the present invention after confirming that the fat-soluble first drug does not have an effect on the hardness of the solid preparation since the fat-soluble first drug does not penetrate a tablet containing the second drug when coating the surface of the solid preparation containing the second drug with an oil-proof material.

DISCLOSURE

Technical Problem

In order to solve the above-described problems, an aspect of the present invention may provide an oral complex preparation comprising: a capsule containing a fat-soluble first drug; and a solid preparation containing a second drug, the solid preparation being embedded into the capsule and including an oil-proof material coating layer on the surface thereof.

Another aspect of the present invention may provide a method of producing an oral complex preparation comprising a solid preparation including an oil-proof material coating layer on the surface thereof, the method comprising: a first step of coating a coating solution including the oil-proof material on the solid preparation, which is contained in a capsule containing a fat-soluble first drug and contains a second drug, thereby preparing a solid preparation coated with the oil-proof material; and a second step of embedding the solid preparation coated with the oil-proof material prepared in the first step into a capsule sheath, injecting the fat-soluble first drug into the solid preparation, and sealing the fat-soluble first drug injected into the solid preparation, thereby preparing a capsule.

Technical Solution

In accordance with an exemplary embodiment of the present invention, an oral complex preparation may include: a capsule containing a fat-soluble first drug; and a solid preparation which is embedded into the capsule, includes an oil-proof material coating layer on the surface thereof, and contains a second drug.

In accordance with another exemplary embodiment of the present invention, a method of producing an oral complex preparation comprising a solid preparation including an oil-proof material coating layer on the surface thereof may include: a first step of coating a coating solution including the oil-proof material on the solid preparation, which is contained in a capsule containing a fat-soluble first drug and contains a second drug, thereby preparing a solid preparation coated with the oil-proof material; and a second step of embedding the solid preparation coated with the oil-proof material prepared in the first step into a capsule sheath, injecting the fat-soluble first drug into the solid preparation, and sealing the fat-soluble first drug injected into the solid preparation, thereby preparing a capsule.

Hereinafter, the present invention will be described in detail.

The present invention relates to an oral complex preparation comprising: a capsule containing a fat-soluble first drug; and a solid preparation containing a second drug, the solid preparation being embedded into the capsule and including an oil-proof material coating layer on the surface thereof, and the complex preparation may be a pharmaceutical complex preparation.

The "capsule" may be a capsule manufactured by encapsulating a medical substance or drug or forming an encapsulating material into a capsule. For example, the capsule may be a preparation in the form of filling a medical substance or drug in a sheath made of material including one or more ingredients selected from the group consisting of starch, gum arabic, tragacanth gum, karaya gum, ghatti gum, guar gum, locust bean gum, tara gum, konjac gum, algin, agar, carrageenan, flurane, pectin, gellan, mannan, glycerin, gelatin, and xanthan gum.

The "solid preparation" may be a solid preparation prepared by adding appropriate additives to the medical substance or drug and compressing the medical substance or drug having the additives added thereto into a predetermined shape. Examples of the solid preparation include tablets, granules, pellets, and the like without limitation, and the examples of the solid preparation are not limited to their sizes or shapes.

For instance, the fat-soluble first drug may be in a liquid phase, and specifically an oil phase. For example, although the fat-soluble first drug may be an omega-3 fatty acid or an alkyl ester thereof, the fat-soluble first drug is not limited thereto. The omega-3 fatty acid or the alkyl ester thereof can function to lower levels of serum triglycerides (TG; neutral fat), lower blood pressures and pulse rates of systole and diastole, and lower activities of a blood coagulating factor VII phospholipid complex while hardly causing any side effects in the human body. In the present specification, the "omega-3 fatty acid" is interchangeably referred to as omega-3 unsaturated fatty acid, omega-3 highly unsaturated fatty acid, and polyunsaturated fatty acid (PUFA), and includes docosahexaenoic acid (DHA), eicosapentaenoic acid (EPA), arachidonic acid (ARA), docosapentaenoic acid, α-linolenic acid, and mixtures thereof. In one embodiment, the omega-3 fatty acid alkyl ester may be an alkyl ester with 1 to 3 carbon atoms, and specifically an ethyl ether. For example, the omega-3 fatty acid alkyl ester may be an ethyl ester of DHA or an ethyl ester of EPA. Although a content of the omega-3 fatty acid or the omega-3 fatty acid alkyl ester is not limited, the content of the omega-3 fatty acid or the omega-3 fatty acid alkyl ester may be 500 mg to 2000 mg, or 950 mg to 1050 mg. An omega-3 fatty acid alkyl ester of 90% or higher is called omega-3-acid ethyl ester 90.

For instance, the second drug may be an HMG-CoA reductase inhibitor. Specifically, the second drug may be a statin-based drug. Examples of the "statin-based drug" may include Atorvastatin, Rosuvastatin, Lovastatin, Simvastatin, Pravastatin, Fluvastatin, Cerivastatin, Pitavastatin, and pharmaceutically acceptable salts thereof, but the examples of the "statin-based drug" are not limited thereto. Specifically, the "statin-based drug" may be Atorvastatin or a salt thereof, or Rosuvastatin or a salt thereof. The complex preparation includes the second drug in a therapeutically effective amount. For instance, although the amount of the second drug may be 5 mg to 40 mg, or may be 5 mg to 20 mg, the amount of the second drug is not limited thereto. Specifically, as Atorvastatin, 5 mg to 20 mg of Atorvastatin or a salt thereof, and as Rosuvastatin, 5 mg to 20 mg of Rosuvastatin or a salt thereof may be included in the second drug of the complex preparation.

The "pharmaceutically acceptable salts" used in the present invention mean salts prepared by conventional methods in the art, and such methods of producing the salts are well known to those skilled in the art.

Specifically, the pharmaceutically acceptable salts include salts derived from the following pharmacologically or physiologically acceptable inorganic acids, organic acids, and bases. However, the pharmaceutically acceptable salts are not limited thereto.

Examples of suitable acids may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzene sulfonic acid, and others.

Examples of the salts derived from suitable bases may include alkali metals, for example, sodium, potassium, and alkali earth metals, for example, calcium and magnesium.

The statin-based drug can slow the production of cholesterol by inhibiting HMG-CoA reductase, which regulates the cholesterol production rate of the body, or can reduce cholesterol by enhancing the capability of the liver to remove low-density lipoprotein (LDL) cholesterol that already exists in the blood. That is, a primary effect of the statin-based drug is lowering LDL cholesterol.

Although the statin-based drug has been known to reduce the risk of coronary heart disease (CHD) to about one third, the statin-based drug has been known to have a limited effect on TG and serum high-density lipoprotein (HDL).

Patients with hypercholesterolemia and mixed dyslipidemia show high levels of LDL and TG. Therefore, it is clear that combined administration of the omega-3 fatty acid or alkyl esters thereof and the statin-based drug can exhibit effects when the omega-3 fatty acid or alkyl esters thereof and the statin-based drug equally show high levels of both LDL and TG.

Therefore, since an oral complex preparation in which the omega-3 fatty acid or alkyl esters thereof and the statin-based drug are combined can not only be expected to exhibit the above-mentioned excellent effects, but also resolve the inconvenience to the patient of having to take two drugs, the oral complex preparation also has an advantage in that medication compliance can be increased.

However, in a complex preparation including two or more active ingredients, there is a possibility that the two drugs may mutually react with each other, and there may be a problem in elution, disintegration, or the like for some ingredients caused by other ingredients. Therefore, it is not easy for an ordinary skilled person to formulate the complex preparation such that the complex preparation can be applied to the human body.

For instance, when a formulation including the omega-3 fatty acid or alkyl esters thereof exists in a core portion of the complex preparation and there is a formulation in which the statin-based drug is arranged on the surface of the core portion, the surface area of the complex preparation is greatly increased compared to general tablets since the statin-based drug required for applying the complex preparation to the human body has to be applied onto the surface of the core portion.

Instability of the statin-based drug due to external environment factors (low pH and the like caused by air containing moisture and $CO_2$) has widely been known in the relevant technical fields. As a contact surface of the statin-based drug with air is increased by the external environmental factors, there may be problems such as drops in stability and content of the statin-based drug, increases in related substances, and others in a pharmaceutical preparation. In the case of medical substances, when the medical substances are not permitted by the authorities due to such problems, there is a problem in that the medical substances cannot be used industrially since it is impossible to place the medical substances on the market.

Meanwhile, since the complex preparation of the present invention can prevent contact of the outside with a first drug by including an oil-proof material coated on the surface of the preparation containing the statin-based drug, the complex preparation of the present invention can block a hardness drop or a disintegration delay of a solid preparation including a second drug due to penetration of the first drug. Therefore, the complex preparation of the present invention is characterized in that an elution pattern of the second drug can be adjusted without interference of the first drug.

The oil-proof material may be a material including a hydroxyl group or a carboxyl group exhibiting hydrophilicity since the oil-proof material has a strong polarity. Non-limiting examples of the oil-proof material include polysaccharides such as polyvinyl alcohol (PVA), poloxamer, polyacetate phthalate, gelatin, mannitol, sucrose, xylitol, and others. The oil-proof material may be an oil-proof polymer.

The oil-proof polymer may have a weight average molecular weight of about 5,000 to 200,000. Specifically, the oil-proof polymer may be an oil-proof polymer having a weight average molecular weight of about 5,000 to 250,000. The oil-proof polymer is not limited thereto. Further, the oil-proof polymer may be an oil-proof polymer having a viscosity of 4.0 mPa·s to 65.0 mPa·s, specifically 4.0 mPa·s to 7.0 mPa·s. When an oil-proof polymer having a molecular weight and/or a viscosity deviating from the above ranges is used, there is a problem in that it is difficult to dissolve the oil-proof polymer in a solvent containing water. Therefore, an inconvenience may be caused in that the oil-proof polymer should be heated to dissolve the oil-proof polymer.

The oil-proof material coating layer may be about 1% to 20% by weight, specifically 1% to 15% by weight or 1% to 10% by weight based on the total weight of the solid preparation. Here, when the oil-proof material coating layer is formed in an amount of less than 1% by weight, the oil-proof material coating layer may be incompletely coated, or oil-proofing properties of the oil-proof material coating layer are remarkably reduced such that it may be difficult to accomplish a desired level of the oil-proofing properties. When the oil-proof material coating layer is formed in an amount of more than 20% by weight, the oil-proof material coating layer may have undesirable effects such as elution delay of the second drug and others.

Further, the oil-proof material coating layer may include an oil-proof material and a plasticizer at a weight ratio of 1:1 to 10:1 or a weight ratio of 2:1 to 4:1.

Examples of the plasticizer may include a single material or a combination of two or more materials selected from the group consisting of glycerin, ethylene glycol, diethylene glycol, propylene glycol, dipropylene glycol, a mixture of glycerin and water, polyethylene glycol, polypropylene glycol, trimethylolpropane, and triethylene glycol. Polyethylene glycol may be used as the plasticizer.

For instance, the plasticizer may have a weight average molecular weight of 300 to 35,000. Specifically, the examples of the plasticizer may include plasticizers having a weight average molecular weight of 1,000 to 8,000, but the examples of the plasticizer are not limited thereto.

The complex preparation may additionally include an additional coating layer formed in a single layer or a plurality of layers inside or outside the oil-proof material coating layer. The additional coating layer may be a film coating layer. The additional coating layer may include OPADRY®, and OPADRY® may be OPADRY® I or OPADRY® II. Specifically, OPADRY® may be OPADRY® OY-C-7000A, a film coating which is manufactured by Colorcon, is composed of 54.85 weight % of hydroxypropylmethyl cellulose, 13.72 weight % of ethylcellulose, 22.86 weight % of titanium oxide, and 8.57 weight % of diethylphthalate.

The complex preparation has a structure in which a solid preparation containing a statin-based drug as a second drug is embedded in (impregnated into) a capsule containing an omega-3 fatty acid or an alkyl ester thereof as a fat-soluble first drug. The solid preparation is embedded in the capsule, and moisture and air of the outside cannot pass through a capsule layer including the omega-3 fatty acid or alkyl esters thereof having lipophilicity. Therefore, the statin-based drug included in the solid preparation can fundamentally block contact with external environmental factors such as moisture, air, and others, and accordingly the statin-based drug may have stability for a long period of time.

Meanwhile, when embedding a statin-based drug such as Atorvastatin, Lovastatin, or the like in a positive state in an omega-3 fatty acid ester, which is a fat-soluble drug, the statin-based drug may be penetrated by the omega-3 fatty acid or an alkyl ester thereof over time. Therefore, in order to overcome this, the complex preparation of the present invention enables an oil-proof material to be coated on the solid preparation containing the second drug such that the complex preparation can block penetration of the above-mentioned omega-3 fatty acid or alkyl esters thereof.

For instance, examples of the solid preparation containing the second drug may include a pharmaceutically acceptable excipient, a binder, a disintegrating agent, a disintegration accelerant, a lubricant, a sustained-release material, a coating agent, a film coating material, an enteric film coating material, a soft capsule material, a soft capsule suspending agent, and others.

The solid preparation may additionally include an excipient. Non-limiting examples of the excipient include starch, pregelatinized starch, microcrystalline cellulose, calcium carbonate, sucrose, lactose, gelatin, mannitol, calcium hydrogen phosphate anhydrous, and others.

The solid preparation may additionally include a binder. Non-limiting examples of the binder include: disaccharides such as sucrose and lactose; polysaccharides including starch, cellulose or a modified cellulose such as microcrystalline cellulose, cellulose ether such as hydroxypropyl cellulose, and the like, and derivatives of the polysaccharides; sugar alcohols such as xylitol, sorbitol, and maltitol; proteins such as gelatin and others; synthetic polymers such as polyvinyl pyrrolidone, polyethylene glycol, and the like; and polysorbate and others.

The solid preparation may additionally include a disintegrating agent. Non-limiting examples of the disintegrating agent include hydroxypropyl methylcellulose, corn starch, agar powder, methylcellulose, bentonite, hydroxypropyl starch, carboxymethylcellulose sodium, sodium alginate, carboxymethylcellulose calcium, calcium citrate, sodium lauryl sulfate, silicic acid anhydride, dextran, ion exchange resin, polyvinyl acetate, formaldehyde-treated casein, amylose, guar gum, polyvinylpyrrolidone, calcium phosphate gelling starch, gum arabic, amylopectin, pectin, sodium polyphosphate, ethyl cellulose, white sugar, magnesium aluminum silicate, D-sorbitol solution, crospovidone, croscarmellose sodium and sodium starch glycolate, and one or a combination of two or more thereof may be used as the disintegrating agent. Specifically, the disintegrating agent may be one or more selected from the group consisting of crospovidone, croscarmellose sodium, and sodium starch glycolate. However, the disintegrating agent is not limited thereto.

The solid preparation may additionally include a lubricant. Non-limiting examples of the lubricant include inorganic matters such as talc, silica, and the like, and fats such as vegetable stearin, magnesium stearate, and stearic acid.

In order to increase the disintegration rate of an oral complex preparation of the present invention, the disintegrating agent may be used in an excess amount. The excess amount means 1% to 20% by weight, specifically 5% to 20% by weight or 5% to 15% by weight based on the total weight of the solid preparation including the statin-based drug.

In one embodiment of the present invention, it has been confirmed that the complex preparation exhibits excellent stability by using as an example of the above-mentioned complex preparation a complex preparation including: a capsule containing an omega-3 fatty acid or an alkyl ester thereof; and a solid preparation containing the statin-based drug (for example, Atorvastatin or Rosuvastatin), the solid preparation being embedded in the capsule and coated with polyvinyl alcohol, which is an oil-proof material, thereby preventing the amount of the statin-based drug contained in the complex preparation from changing under various temperature and humidity conditions for a long storage period.

In general, although elution of the solid preparation is rapid when the disintegrating agent is used in an excess amount, there is a possibility that the disintegrating agent may have an effect on stability of the solid preparation by drawing in moisture from the air. However, in the case of the oral complex preparation of the present invention, the solid preparation containing the statin-based drug is embedded in the capsule containing the omega-3 fatty acid or the alkyl ester thereof. Therefore, the disintegrating agent does not have an effect on the stability of the solid preparation since the solid preparation is completely blocked from moisture, even though the disintegrating agent is used in an excess amount.

As described above, the complex preparation of the present invention is disintegrated and/or eluted within an appropriate time range to be able to prevent occurrence of a problem wherein the statin-based drug is exposed to acid located on the statin-based drug when the complex preparation is disintegrated and/or eluted within a very short period of time.

Further, a formulation structure of the oral complex preparation of the present invention does not have any negative effects on the action in the body and effectiveness exhibited by the omega-3 fatty acid or the alkyl ester thereof and the statin-based drug, i.e., the effective drugs.

In one embodiment, an amount of the omega-3 fatty acid or the alkyl ester thereof included in the oral complex preparation of the present invention may be about 20% to 90% by weight, specifically about 30% to 80% by weight or about 35% to 75% by weight with respect to the total weight of the oral complex preparation. More specifically, there is a disadvantage in that a sufficient therapeutic effect is not obtained when the amount of the omega-3 fatty acid or the alkyl ester thereof is less than 20% by weight with respect to the total weight of the oral complex preparation, and there is a disadvantage in that convenience in taking medicine orally is reduced due to an increase in the size of a manufactured soft capsule when the amount of the omega-3 fatty acid or the alkyl ester thereof is more than 90% by weight.

In one embodiment, an amount of the statin-based drug included in the oral complex preparation of the present invention may be 0.3% to 20% by weight, specifically 0.3% to 10% by weight with respect to the total weight of the oral complex preparation. There is a disadvantage in that a sufficient therapeutic effect is not obtained when the amount of the statin-based drug is less than 0.3% by weight with respect to the total weight of the oral complex preparation, and side effects may occur due to excessive medication when the amount of the statin-based drug is more than 20% by weight.

Further, the complex preparation may be prepared by a method comprising: a first step of coating a coating solution including the oil-proof material on the solid preparation, which is contained in a capsule containing a fat-soluble first drug and contains a second drug, thereby preparing a solid preparation coated with the oil-proof material; and a second step for preparing a capsule by embedding the solid preparation coated with the oil-proof material prepared in the first step into a capsule sheath, injecting the fat-soluble first drug into the capsule, and sealing the capsule.

At this time, the coating solution may include an aqueous solution obtained by dissolving polyvinyl alcohol as the oil-proof material, polyethylene glycol (for example, PEG6000) as a plasticizer, and others in a solvent containing water. However, the coating solution is not limited thereto.

Advantageous Effects

An oral complex preparation of the present invention comprising: a capsule containing a fat-soluble first drug; and a solid preparation containing a second drug, the solid preparation being embedded into the capsule and including an oil-proof material coating layer on the surface thereof, can be used in simultaneously administering two kinds of drugs. At this time, the oil-proof material coating layer on the surface of the solid preparation can block penetration of the fat-soluble first drug into the solid preparation containing the second drug. Therefore, the oil-proof material coating layer not only prevents an inadequate reaction of the first drug and the second drug, but also enables hardness of the solid preparation to be maintained for an adequate time and enables disintegration time not to be delayed without the solid preparation itself containing the second drug being penetrated by the first drug.

BRIEF DESCRIPTION OF THE DRAWINGS

FIG. 1 is a drawing showing a photograph of an oral complex preparation prepared according to an embodiment of the present invention.

BEST MODE

Hereinafter, the present invention will be described in more detail through examples. The following examples are provided to elucidate the present invention, but should not be construed as limiting.

Example 1: Production of an Oral Complex Preparation Containing Atorvastatin (1)

<Production of Atorvastatin Film-Coated Tablets>

After mixing Atorvastatin calcium trihydrate, microcrystalline cellulose, calcium carbonate, croscarmellose sodium, sodium starch glycolate, and pregelatinized starch using the composition described in Table 1 in a mixer to obtain a mixture, mixing the mixture with a binder solution (binder: polysorbate 80, solvent: purified water) to obtain a binder solution-mixed mixture, granulating the binder solution-mixed mixture in a speedmixer granulator to obtain a granule, drying the granule at 50° C. for 8 hours in a dryer to obtain a dried granule, oscillating the dried granule using a power mill oscillator, and a post-mixing croscarmellose sodium, hydroxypropyl cellulose, and colloidal silicon dioxide with the oscillated granule to obtain a mixture, the mixture was tableted by a rotary tablet press with adding magnesium stearate. Thereafter, OPADRY® (OY-C-7000A)

and an ethanol-mixed solution (ethanol:purified water=8:2) were mixed to prepare a coating solution, the tablet-pressed solid preparation was coated with the coating solution, and the tablet-pressed solid preparation coated with the coating solution was dried to produce an Atorvastatin film-coated tablet. An Atorvastatin film-coated tablet coated with the oil-proof material was prepared by mixing polyvinyl alcohol, polyethylene glycol 6000, and purified water to prepare an oil-proof coating solution and coating the Atorvastatin film-coated tablet with the oil-proof coating solution.

<Embedment of Atorvastatin Film-Coated Tablet and Formation of Soft Capsule>

Then, after enabling a soft capsule film-manufacturing machine to manufacture a soft capsule film using gelatin and concentrated glycerin, and embedding omega-3 fatty acid ethyl ester 90 as a liquid content and the Atorvastatin film-coated tablet coated with the oil-proof material into a soft capsule, an omega-3 fatty acid ethyl ester 90 soft capsule coated with the oil-proof material was prepared by a rotary production method using tablet-soft capsule-forming equipment.

Example 2: Production of an Oral Complex Preparation Containing Atorvastatin (2)

A complex preparation of Example 2 was prepared in accordance with Table 1 using the production method of Example 1.

Example 3: Production of an Oral Complex Preparation Containing Atorvastatin (3)

A complex preparation of Example 3 was prepared in accordance with Table 1 using the production method of Example 1. Specifically, the complex preparation of Example 3 was prepared in the same manner as in Example 1 except that the OPADRY® coating layer was not included.

Example 4: Production of an Oral Complex Preparation Containing Atorvastatin (4)

A complex preparation of Example 4 was prepared in accordance with Table 1 using the production method of Example 1. Specifically, the complex preparation of Example 4 was prepared in the same manner as in Example 1 except that the OPADRY® coating layer and PEG 6000 as a plasticizer were not included.

Example 5: Production of an Oral Complex Preparation Containing Atorvastatin (5)

A complex preparation of Example 5 was prepared in accordance with Table 1 using the production method of Example 1. Specifically, the complex preparation of Example 5 was prepared in the same manner as in Example 1 except that PEG 6000 as the plasticizer was not included.

Example 6: Production of an Oral Complex Preparation Containing Atorvastatin (6)

A complex preparation of Example 6 was prepared in accordance with Table 1 using the production method of Example 1. Specifically, the complex preparation of Example 6 was prepared in the same manner as in Example 1 except that the content of PEG 6000 as the plasticizer was decreased.

Example 7: Production of an Oral Complex Preparation Containing Atorvastatin (7)

A complex preparation of Example 7 was prepared in accordance with Table 1 using the production method of Example 1. Specifically, the complex preparation of Example 7 was prepared in the same manner as in Example 1 except that the content of PEG 6000 as the plasticizer was increased.

Comparative Example 1

A complex preparation of Comparative Example 1 was prepared in the same manner as in Example 1 except that the processes of primarily coating and secondarily coating the solid preparation were omitted in Example 1.

Comparative Example 2

A complex preparation of Comparative Example 2 was prepared in the same manner as in Example 1 except that the process of coating the solid preparation with polyvinyl alcohol was omitted in Example 1.

TABLE 1

| Classification | Ingredients | Example 1 | Example 2 | Example 3 | Example 4 | Example 5 | Example 6 | Example 7 | Comparative Example 1 | Comparative Example 2 |
|---|---|---|---|---|---|---|---|---|---|---|
| Tablet part containing a statin-based drug | Atorvastatin calcium trihydrate | 10.85 | 20.72 | 10.85 | 10.85 | 10.85 | 10.85 | 10.85 | 10.85 | 10.85 |
| | Microcrystalline cellulose | 19.60 | 14.73 | 19.60 | 19.60 | 19.60 | 19.60 | 19.60 | 19.60 | 19.60 |
| | Pregelatinized starch | 20.00 | 15.00 | 20.00 | 20.00 | 20.00 | 20.00 | 20.00 | 20.00 | 20.00 |
| | Calcium carbonate | 33.00 | 33.00 | 33.00 | 33.00 | 33.00 | 33.00 | 33.00 | 33.00 | 33.00 |
| | Croscarmellose sodium | 8.00 | 8.00 | 8.00 | 8.00 | 8.00 | 8.00 | 8.00 | 8.00 | 8.00 |
| | Sodium starch glycolate | 5.00 | 5.00 | 5.00 | 5.00 | 5.00 | 5.00 | 5.00 | 5.00 | 5.00 |
| | Polysorbate 80 | 0.40 | 0.40 | 0.40 | 0.40 | 0.40 | 0.40 | 0.40 | 0.40 | 0.40 |
| | Hydroxypropyl cellulose | 2.00 | 2.00 | 2.00 | 2.00 | 2.00 | 2.00 | 2.00 | 2.00 | 2.00 |
| | Magnesium stearate | 0.50 | 0.50 | 0.50 | 0.50 | 0.50 | 0.50 | 0.50 | 0.50 | 0.50 |
| | Colloidal silicon dioxide | 0.65 | 0.65 | 0.65 | 0.65 | 0.65 | 0.65 | 0.65 | 0.65 | 0.65 |
| Primary table coating part | Opadry (OY-C-7000A) | 3.00 | 3.00 | 0 | 0 | 3.00 | 3.00 | 3.00 | 0 | 3.00 |
| Secondary | Polyvinyl | 3.00 | 3.00 | 3.00 | 3.00 | 3.00 | 3.00 | 3.00 | 0 | 0 |

TABLE 1-continued

| Classification | Ingredients | Example 1 | Example 2 | Example 3 | Example 4 | Example 5 | Example 6 | Example 7 | Comparative Example 1 | Comparative Example 2 |
|---|---|---|---|---|---|---|---|---|---|---|
| table coating part | alcohol PEG 6000 | 1.00 | 1.00 | 1.00 | 0 | 0 | 0.50 | 1.50 | 0 | 0 |
| Capsule liquid content | Omega-3 ethyl ester 90 | 1,000 | 1,000 | 1,000 | 1,000 | 1,000 | 1,000 | 1,000 | 1,000 | 1,000 |
| Capsule shell | Gelatin | 293.00 | 293.00 | 293.00 | 293.00 | 293.00 | 293.00 | 293.00 | 293.00 | 293.00 |
| | Concentrated glycerin | 135.00 | 135.00 | 135.00 | 135.00 | 135.00 | 135.00 | 135.00 | 135.00 | 135.00 |
| Total | | 1,535.00 | 1,535.00 | 1,532.00 | 1,531.00 | 1,534.00 | 1,534.50 | 1,535.50 | 1,528.00 | 1,531.00 |

Example 8: Production of an Oral Complex Preparation Containing Rosuvastatin (1)

<Production of Rosuvastatin Film-Coated Tablet>

According to the amounts described in Table 2, calcium rosuvastatin and calcium hydrogen phosphate anhydrous were mixed, followed by mixing with microcrystalline cellulose, lactose hydrate, and crospovidone. Magnesium stearate was then added to the resulting mixture to be tableted by a tablet press. Thereafter, polyvinyl alcohol (PVA) was mixed with water to prepare a coating solution, the tablet-pressed solid preparation was additionally coated with OPADRY® using the coating solution, and the tablet-pressed solid preparation coated with OPADRY® was dried to prepare a Rosuvastatin film-coated tablet. Thereafter, OPADRY® (OY-C-7000A) and an ethanol-mixed solution (ethanol:purified water=8:2) were mixed to prepare a coating solution, the tablet-pressed solid preparation was coated with the coating solution, and the tablet-pressed solid preparation coated with the coating solution was dried to produce the Rosuvastatin film-coated tablet. A Rosuvastatin film-coated tablet coated with the oil-proof material was prepared by mixing polyvinyl alcohol, polyethylene glycol 6000, and purified water to prepare an oil-proof coating solution and coating the Rosuvastatin film-coated tablet with the oil-proof coating solution.

<Embedment of Rosuvastatin Film-Coated Tablet and Formation of Soft Capsule>

Then, after enabling a soft capsule film-manufacturing machine to manufacture a soft capsule film using gelatin and concentrated glycerin, and embedding omega-3 fatty acid ethyl ester 90 as a liquid content and the Rosuvastatin film-coated tablet coated with the oil-proof material into a soft capsule, an omega-3 fatty acid ethyl ester 90 soft capsule coated with the oil-proof material was prepared by a rotary production method using tablet-soft capsule-forming equipment.

Example 9: Production of an Oral Complex Preparation Containing Atorvastatin (2)

A complex preparation of Example 9 was prepared in accordance with Table 2 using the production method of Example 8.

Example 10: Production of an Oral Complex Preparation Containing Atorvastatin (3)

A complex preparation of Example 10 was prepared in accordance with Table 2 using the production method of Example 8. Specifically, the complex preparation of Example 10 was prepared in the same manner as in Example 8 except that the OPADRY® coating layer was not included.

Example 11: Production of an Oral Complex Preparation Containing Atorvastatin (4)

A complex preparation of Example 11 was prepared in accordance with Table 2 using the production method of Example 8. Specifically, the complex preparation of Example 11 was prepared in the same manner as in Example 8 except that the OPADRY® coating layer and PEG 6000 as a plasticizer were not included.

Example 12: Production of an Oral Complex Preparation Containing Atorvastatin (5)

A complex preparation of Example 12 was prepared in accordance with Table 2 using the production method of Example 8. Specifically, the complex preparation of Example 12 was prepared in the same manner as in Example 8 except that PEG 6000 as the plasticizer was not included.

Example 13: Production of an Oral Complex Preparation Containing Atorvastatin (6)

A complex preparation of Example 13 was prepared in accordance with Table 2 using the production method of Example 8. Specifically, the complex preparation of Example 13 was prepared in the same manner as in Example 8 except that the content of polyvinyl alcohol as the oil-proof material was increased.

Example 14: Production of an Oral Complex Preparation Containing Atorvastatin (7)

A complex preparation of Example 14 was prepared in accordance with Table 2 using the production method of Example 8. Specifically, the complex preparation of Example 14 was prepared in the same manner as in Example 8 except that the content of PEG 6000 as the plasticizer was increased.

Comparative Example 3

A complex preparation of Comparative Example 3 was prepared in the same manner as in Example 8 except that the processes of primarily coating and secondarily coating the solid preparation were omitted in Example 8.

Comparative Example 4

A complex preparation of Comparative Example 4 was prepared in the same manner as in Example 8 except that the process of coating the solid preparation with polyvinyl alcohol was omitted in Example 8.

TABLE 2

| Classification | Ingredients | Example 8 | Example 9 | Example 10 | Example 11 | Example 12 | Example 13 | Example 14 | Comparative Example 3 | Comparative Example 4 |
|---|---|---|---|---|---|---|---|---|---|---|
| Tablet part containing a statin-based drug | Rosuvastatin calcium | 5.20 | 10.40 | 5.20 | 5.20 | 5.20 | 5.20 | 5.20 | 5.20 | 5.20 |
| | Lactose hydrate | 37.00 | 37.00 | 37.00 | 37.00 | 37.00 | 37.00 | 37.00 | 37.00 | 37.00 |
| | Microcrystalline cellulose | 36.00 | 30.80 | 36.00 | 36.00 | 36.00 | 36.00 | 36.00 | 36.00 | 36.00 |
| | Calcium hydrogen phosphate anhydrous | 10.90 | 10.90 | 10.90 | 10.90 | 10.90 | 10.90 | 10.90 | 10.90 | 10.90 |
| | Crospovidone | 9.00 | 9.00 | 9.00 | 9.00 | 9.00 | 9.00 | 9.00 | 9.00 | 9.00 |
| | Magnesium stearate | 1.50 | 1.50 | 1.50 | 1.50 | 1.50 | 1.50 | 1.50 | 1.50 | 1.50 |
| Primary table coating part | Opadry (OY-C-7000A) | 3.00 | 3.00 | 0 | 0 | 3.00 | 3.00 | 3.00 | 0 | 3.00 |
| Secondary table coating part | Polyvinyl alcohol | 3.00 | 3.00 | 3.00 | 3.00 | 3.00 | 6.00 | 3.00 | 0 | 0 |
| | PEG 6000 | 1.00 | 1.00 | 1.00 | 0 | 0 | 1.00 | 1.50 | 0 | 0 |
| Capsule liquid content | Omega-3 ethyl ester 90 | 1,000 | 1,000 | 1,000 | 1,000 | 1,000 | 1,000 | 1,000 | 1,000 | 1,000 |
| Capsule shell | Gelatin | 293.00 | 293.00 | 293.00 | 293.00 | 293.00 | 293.00 | 293.00 | 293.00 | 293.00 |
| | Concentrated glycerin | 135.00 | 135.00 | 135.00 | 135.00 | 135.00 | 135.00 | 135.00 | 135.00 | 135.00 |
| Total | | 1,534.60 | 1,534.60 | 1,531.60 | 1,530.60 | 1,533.60 | 1,537.60 | 1,535.10 | 1,527.60 | 1,530.60 |

Experimental Example 1. Disintegration Test of Tablet Containing Atorvastatin

In order to check disintegration times of the prepared complex preparations of Examples 1 to 7 and the prepared tablets of Comparative Examples 1 and 2, the disintegration times were measured in water having a temperature of 37±2° C. in accordance with a general disintegration test method of the Korean Pharmacopoeia.

According to the disintegration test method, as a test method of checking if the tablets were disintegrated in a test liquid within regular hours under predetermined conditions, each specimen was put into glass tubes of six testers, and the testers were operated at 37° C. using water as the test liquid. The complex preparations and the tablets were determined to be suitable when all of the specimens were disintegrated by observing disintegration conditions of the specimens. When one or two specimens were not disintegrated, 12 specimens were tested again such that the complex preparations and the tablets were determined to be suitable when 16 specimens or more among the total 18 specimens were disintegrated. All tablets sealed with an omega-3 oil phase and stored in a light shading state were used.

TABLE 3

| Disintegration time | Comparative Example 1 | Comparative Example 2 | Example 1 | Example 2 | Example 3 | Example 4 | Example 5 | Example 6 | Example 7 |
|---|---|---|---|---|---|---|---|---|---|
| 0 weeks | <1 minute and 30 seconds | <1 minute and 30 seconds | <1 minute and 20 seconds | <1 minute and 30 seconds | <1 minute and 40 seconds | <1 minute and 50 seconds | <1 minute and 50 seconds | <1 minute and 35 seconds | <1 minute and 35 seconds |
| 2 weeks | <4 minutes and 10 seconds | <4 minutes and 20 seconds | <1 minute and 40 seconds | <1 minute and 45 seconds | <3 minutes and 10 seconds | <3 minutes and 20 seconds | <2 minutes and 10 seconds | <2 minutes and 05 seconds | <1 minute and 40 seconds |
| 4 weeks | <5 minutes and 30 seconds | <5 minutes and 20 seconds | <1 minute and 40 seconds | <1 minute and 35 seconds | <3 minutes and 50 seconds | <3 minutes and 55 seconds | <2 minutes and 20 seconds | <2 minutes and 10 seconds | <1 minute and 45 seconds |
| 6 weeks | <7 minutes and 40 seconds | <7 minutes and 10 seconds | <1 minute and 40 seconds | <1 minute and 55 seconds | <5 minutes and 50 seconds | <6 minutes and 10 seconds | <2 minutes and 25 seconds | <2 minute and 15 seconds | <1 minute and 45 seconds |
| 8 weeks | <8 minutes and 20 seconds | <7 minutes and 40 seconds | <1 minute and 50 seconds | <1 minute and 45 seconds | <6 minutes and 30 seconds | <6 minutes and 45 seconds | <2 minutes and 30 seconds | <2 minutes and 20 seconds | <1 minute and 50 seconds |

TABLE 3-continued

| Disintegration time | Comparative Example 1 | Comparative Example 2 | Example 1 | Example 2 | Example 3 | Example 4 | Example 5 | Example 6 | Example 7 |
|---|---|---|---|---|---|---|---|---|---|
| 12 weeks | <8 minutes and 50 seconds | <8 minutes and 30 seconds | <1 minute and 50 seconds | <1 minute and 55 seconds | <7 minutes and 20 seconds | <7 minutes and 35 seconds | <2 minutes and 40 seconds | <2 minutes and 25 seconds | <1 minute and 55 seconds |

As shown in Table 3, it could be confirmed in Comparative Example 1, of an uncoated Atorvastatin tablet which had not been coated, and Comparative Example 2, of an Atorvastatin tablet which had been coated with OPADRY® only, that disintegration times of the tablets were delayed as an omega-3 oil was absorbed into the tablets during the storage of the tablets.

However, the tablets of Examples 1 to 7 including a coating layer containing polyvinyl alcohol according to the present invention exhibited certain disintegration times even when storage times of the tablets had elapsed. This shows that the tablets can be maintained in a stable state without being influenced by oily ingredients by enabling the coating layer containing polyvinyl alcohol to inhibit absorption of omega-3 oil into the tablets.

Therefore, the tablet including the coating layer containing polyvinyl alcohol can block a physiochemical reaction of an omega-3 oil of an oil phase with respect to the tablets.

Experimental Example 2. Disintegration Test of Tablet Containing Rosuvastatin

In order to check disintegration times of the prepared complex preparations of Examples 8 to 14 and the prepared tablets of Comparative Examples 3 and 4, the disintegration times were measured in a pH 1.2 aqueous solution of 37±2° C. in accordance with a general disintegration test method of the Korean Pharmacopoeia.

According to the disintegration test method, as a test method of checking if the tablets were disintegrated in a test liquid within regular hours in predetermined conditions, each specimen was put into glass tubes of six testers, and the testers were operated at 37° C. using water as the test liquid. The complex preparations and the tablets were determined to be suitable when all of the specimens were disintegrated by observing disintegration conditions of the specimens. When one or two specimens were not disintegrated, 12 specimens were tested again such that the complex preparations and the tablets were determined to be suitable when 16 specimens or more among the total 18 specimens were disintegrated. All tablets sealed with an omega-3 oil phase and stored in a light shading state were used.

TABLE 4

| Disintegration time | Comparative Example 3 | Comparative Example 4 | Example 8 | Example 9 | Example 10 | Example 11 | Example 12 | Example 13 | Example 14 |
|---|---|---|---|---|---|---|---|---|---|
| 0 weeks | <1 minute | <1 minute and 30 seconds | <1 minute and 30 seconds | <1 minute and 20 seconds | <1 minute and 30 seconds | <1 minute and 40 seconds | <1 minute and 45 seconds | <1 minute and 45 seconds | <1 minute and 40 seconds |
| 2 weeks | <3 minutes and 50 seconds | <4 minutes and 10 seconds | <1 minute and 45 seconds | <1 minute and 40 seconds | <3 minutes and 20 seconds | <3 minutes and 10 seconds | <2 minutes and 15 seconds | <2 minutes and 10 seconds | <1 minute and 45 seconds |
| 4 weeks | <5 minutes and 20 seconds | <5 minutes and 35 seconds | <1 minute and 45 seconds | <1 minute and 35 seconds | <4 minutes and 10 seconds | <3 minutes and 50 seconds | <2 minutes and 25 seconds | <2 minutes and 10 seconds | <1 minute and 45 seconds |
| 6 weeks | <7 minutes and 30 seconds | <7 minutes and 25 seconds | <1 minute and 50 seconds | <1 minute and 55 seconds | <5 minutes and 40 seconds | <5 minutes and 55 seconds | <2 minutes and 30 seconds | <2 minute and 15 seconds | <1 minute and 50 seconds |
| 8 weeks | <8 minutes and 30 seconds | <8 minutes | <1 minute and 50 seconds | <1 minute and 45 seconds | <6 minutes and 20 seconds | <6 minutes and 40 seconds | <2 minutes and 30 seconds | <2 minutes and 25 seconds | <1 minute and 50 seconds |
| 12 weeks | <8 minutes and 40 seconds | <8 minutes and 30 seconds | <1 minute and 50 seconds | <1 minute and 55 seconds | <7 minutes and 10 seconds | <7 minutes and 25 seconds | <2 minutes and 40 seconds | <2 minutes and 25 seconds | <1 minute and 55 seconds |

As shown in Table 4, it could be confirmed in Comparative Example 3, of an uncoated Rosuvastatin tablet which had not been coated, and Comparative Example 4, of a Rosuvastatin tablet which had been coated with OPADRY® only, that disintegration times of the tablets were delayed as an omega-3 oil was absorbed into the tablets during the storage of the tablets.

However, the tablets of Examples 8 to 14 including a coating layer containing polyvinyl alcohol according to the present invention exhibited certain disintegration times even when storage times of the tablets had elapsed. This shows that the tablets can be maintained in a stable state without being influenced by oily ingredients by enabling the coating layer containing polyvinyl alcohol to inhibit absorption of an omega-3 oil into the tablets.

Therefore, the tablet including the coating layer containing polyvinyl alcohol can block a physiochemical reaction of an omega-3 oil of an oil phase with respect to the tablets.

Experimental Example 3: Hardness Test of a Tablet Containing Atorvastatin omega-3 oil conditions for 6 months. As the control group, weight of the Atorvastatin tablet was measured after performing an oil-proof coating process in Example 1 to prepare an Atorvastatin tablet, and sealing and storing the Atorvastatin tablet at room temperature without storing the Atorvastatin tablet in omega-3 oil. As a result, it was confirmed that weight of the tablet was increased as much as about 10% compared to the weight of the tablet immediately after the production. This shows that omega-3 had penetrated into the relevant tablet. Further, it was confirmed that after storing the tablets of Comparative Examples 1 and 2 for 6 months, hardness values of the tablets were remarkably lowered compared to immediately after the production. This aso shows that omega-3 had penetrated into the tablets.

In contrast, even when measuring weights of the tablets after sealing and storing the tablets of the control group and Examples 1 to 7 under the omega-3 oil conditions for 6 months, there were no large differences between the mea-

TABLE 5

| Classification | Control group | Comparative Example 1 | Comparative Example 2 | Example 1 | Example 2 |
|---|---|---|---|---|---|
| Storage conditions | Sealing at room temperature | | | | |
| Tablet weight (after production) | 107 ± 1 mg (n = 3/e arc case) | 100 ± 1 mg (n = 3/e arc case) | 103 ± 1 mg (n = 3/e arc case) | 107 ± 1 mg (n = 3/e arc case) | 107 ± 1 mg (n = 3/e arc case) |
| Tablet weight change 6 months (after storage) | 107.4 | 110.9 | 113.2 | 107.2 | 107.2 |
| Tablet hardness (after production) | 7.0~8.0 kg/f | 7.0~8.0 kg/f | 7.0~8.0 kg/f | 7.0~8.0 kg/f | 7.0~8.0 kg/f |
| Tablet hardness change (6 months after storage) | 7.0~8.0 kg/f | 2.0~3.0 kg/f | 4.0~5.0 kg/f | 7.0~8.0 kg/f | 7.0~8.0 kg/f |

| Classification | Example 3 | Example 4 | Example 5 | Example 6 | Example 7 |
|---|---|---|---|---|---|
| Storage conditions | Sealing in omega-3 | | | | |
| Tablet weight (after production) | 104 ± 1 mg (n = 3/e arc case) | 103 ± 1 mg (n = 3/e arc case) | 106 ± 1 mg (n = 3/e arc case) | 110 ± 1 mg (n = 3/e arc case) | 107.5 ± 1 mg (n = 3/e arc case) |
| Tablet weight change 6 months (after storage) | 110.5 | 111.1 | 109.2 | 110.9 | 107.5 |
| Tablet hardness (after production) | 7.0~8.0 kg/f | 7.0~8.0 kg/f | 7.0~8.0 kg/f | 7.0~8.0 kg/f | 7.0~8.0 kg/f |
| Tablet hardness change (6 months after storage) | 4.5~5.5 kg/f | 4.5~5.5 kg/f | 6.5~7.5 kg/f | 6.5~7.5 kg/f | 7.0~8.0 kg/f |

Measured weight changes and hardness changes of the preparations of Comparative Examples 1 and 2 and Examples 1 to 7 are compared and shown in Table 5. A hardness test was used to measure hardness values of the preparations, and an average value of the hardness values was listed using 6 specimens. In Comparative Examples 1 and 2 of Table 5, weights of the Atorvastatin tablets were measured after sealing and storing Atorvastatin tablets under sured weights of the tablets and measured weight values of the tablets immediately after the production. This was determined to be because the tablets of Examples 1 to 7 have oil-proofing properties.

Experimental Example 4: Hardness Test of a Tablet Containing Rosuvastatin

TABLE 6

| Classification | Control group | Comparative Example 3 | Comparative Example 4 | Example 8 | Example 9 |
|---|---|---|---|---|---|
| Storage conditions | Sealing at room temperature | | | | |
| Tablet weight (after production) | 107.6 ± 1 mg (n = 3/e arc case) | 100.6 ± 1 mg (n = 3/e arc case) | 103.6 ± 1 mg (n = 3/e arc case) | 107.6 ± 1 mg (n = 3/e arc case) | 107.6 ± 1 mg (n = 3/e arc case) |

TABLE 6-continued

| | | | | | |
|---|---|---|---|---|---|
| Tablet weight change 6 months (after storage) | 107.3 | 112.9 | 111.2 | 107.3 | 107.4 |
| Tablet hardness (after production) | 7.0~8.0 kg/f | 7.0~8.0 kg/f | 7.0~8.0 kg/f | 7.0~8.0 kg/f | 7.0~8.0 kg/f |
| Tablet hardness change (6 months after storage) | 7.0~8.0 kg/f | 2.0~3.0 kg/f | 4.0~5.0 kg/f | 7.0~8.0 kg/f | 7.0~8.0 kg/f |

| Classification | Example 10 | Example 11 | Example 12 | Example 13 | Example 14 |
|---|---|---|---|---|---|
| Storage conditions | Sealing in omega-3 | | | | |
| Tablet weight (after production) | 104.6 ± 1 mg (n = 3/e arc case) | 103.6 ± 1 mg (n = 3/e arc case) | 106.6 ± 1 mg (n = 3/e arc case) | 110.6 ± 1 mg (n = 3/e arc case) | 108.1 ± 1 mg (n = 3/e arc case) |
| Tablet weight change 6 months (after storage) | 110.8 | 110.9 | 108.7 | 110.9 | 108.1 |
| Tablet hardness (after production) | 7.0~8.0 kg/f | 7.0~8.0 kg/f | 7.0~8.0 kg/f | 7.0~8.0 kg/f | 7.0~8.0 kg/f |
| Tablet hardness change (6 months after storage) | 4.5~5.5 kg/f | 4.5~5.5 kg/f | 6.5~7.5 kg/f | 6.5~7.5 kg/f | 7.0~8.0 kg/f |

Measured weight changes and hardness changes of the preparations of Comparative Examples 3 and 4 and Examples 8 to 14 are compared and shown in Table 6. A hardness test was used to measure hardness values of the preparations, and an average value of the hardness values was listed using 6 specimens. In Comparative Examples 3 and 4 of Table 6, weights of the tablets were measured after sealing and storing the tablets under omega-3 oil conditions for 6 months. As the control group, weight of the Rosuvastatin tablet was measured after performing an oil-proof coating process in Example 8 to prepare an Rosuvastatin tablet, and sealing and storing the Rosuvastatin tablet at room temperature without storing the Rosuvastatin tablet in omega-3 oil. As a result, it was confirmed that weight of the tablet was increased as much as about 10% compared to the weight of the tablet immediately after the production. This shows that omega-3 had penetrated into the relevant tablet. Further, it was confirmed that after storing the tablets of Comparative Examples 3 and 4 for 6 months, hardness values of the tablets were remarkably lowered compared to immediately after the production. This also shows that omega-3 had penetrated into the tablets.

In contrast, even when measuring weights of the tablets after sealing and storing the tablets of the control group and Examples 8 to 14 under the omega-3 oil conditions for 6 months, there were no large differences between the measured weights of the tablets and measured weight values of the tablets immediately after the production. This was determined to be because the tablets of Examples 8 to 14 have oil-proofing properties.

The above-disclosed subject matter is to be considered illustrative, and not restrictive, and the appended claims are intended to cover all such modifications, enhancements, and other embodiments which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. An oral complex preparation comprising:
   a capsule containing a fat-soluble first drug; and
   a solid preparation containing a second drug, the solid preparation being embedded into the capsule and including an oil-proof material coating layer on the surface thereof,
   wherein the oil-proof material coating layer is included on the solid preparation in an amount of 3% to 6% by weight based on the total weight of the solid preparation;
   wherein the oil-proof material comprises polyvinyl alcohol (PVA);
   wherein the solid preparation further includes an additional coating layer comprising OPADRY® OY-C-7000A formed inside the oil-proof material coating layer; and
   wherein the OPADRY® OY-C-7000A is composed of 54.85 weight % of hydroxypropylmethyl cellulose, 13.72 weight % of ethylcellulose, 22.86 weight % of titanium oxide, and 8.57 weight % of diethylphthalate.

2. The oral complex preparation of claim 1, wherein the fat-soluble first drug is an omega-3 fatty acid or an alkyl ester thereof.

3. The oral complex preparation of claim 1, wherein the oil-proof material further comprises one or more selected from the group consisting of poloxamer, polyacetate phthalate, gelatin, mannitol, sucrose, and xylitol.

4. The oral complex preparation of claim 1, wherein the oil-proof material coating layer additionally includes a plasticizer.

5. The oral complex preparation of claim 4, wherein the plasticizer is polyethylene glycol.

6. The oral complex preparation of claim 4, wherein the oil-proof material coating layer includes an oil-proof material and a plasticizer at a weight ratio of 1:1 to 10:1.

7. The oral complex preparation of claim 1, wherein the second drug is a statin-based drug.

8. The oral complex preparation of claim 7, wherein the statin-based drug is one or more selected from the group consisting of atorvastatin, rosuvastatin, lovastatin, simvastatin, pravastatin, fluvastatin, cerivastatin, pitavastatin, and pharmaceutically acceptable salts thereof.

9. The oral complex preparation of claim 1, wherein the solid preparation containing the second drug further includes a disintegrating agent.

10. The oral complex preparation of claim 9, wherein the disintegrating agent is one or more selected from the group consisting of hydroxypropyl methylcellulose, corn starch, agar powder, methylcellulose, bentonite, hydroxypropyl starch, carboxymethylcellulose sodium, sodium alginate, carboxymethylcellulose calcium, calcium citrate, sodium lauryl sulfate, silicic acid anhydride, dextran, ion exchange resin, polyvinyl acetate, formaldehyde-treated casein, amylose, guar gum, polyvinylpyrrolidone, calcium phosphate gelling starch, gum arabic, amylopectin, pectin, sodium polyphosphate, ethyl cellulose, white sugar, magnesium aluminum silicate, D-sorbitol solution, crospovidone, croscarmellose sodium, and sodium starch glycolate.

11. The oral complex preparation of claim 9, wherein the disintegrating agent is one or more selected from the group consisting of crospovidone, croscarmellose sodium, and sodium starch glycolate.

12. The oral complex preparation of claim 9, wherein the disintegrating agent is included in the solid preparation in an amount of 1% to 20% by weight based on the total weight of the solid preparation.

13. The oral complex preparation of claim 1, wherein the capsule has a sheath made of one or more ingredients selected from the group consisting of starch, gum arabic, tragacanth gum, karaya gum, ghatti gum, guar gum, locust bean gum, tara gum, konjac gum, algin, agar, carrageenan, flurane, pectin, gellan, mannan, glycerin, gelatin, and xanthan gum.

14. A method of producing an oral complex preparation comprising a solid preparation including an oil-proof material coating layer on the surface thereof, the method including:
a first step of coating a first coating solution including OPADRY® OY-C-7000A on the solid preparation;
a second step of coating a second coating solution including the oil-proof material on the solid preparation, which is coated with the first coating solution and contained in a capsule containing a fat-soluble first drug and contains a second drug, thereby preparing a solid preparation coated with the oil-proof material; and
a third step for preparing a capsule by embedding the solid preparation coated with the oil-proof material prepared in the second step into a capsule sheath, injecting the fat-soluble first drug into the capsule, and sealing the capsule,
wherein the oil-proof material coating layer is included on the solid preparation in an amount of 3% to 6% by weight based on the total weight of the solid preparation,
wherein the oil-proof material comprises polyvinyl alcohol (PVA), and
wherein the OPADRY® OY-C-7000A is composed of 54.85 weight % of hydroxypropylmethyl cellulose, 13.72 weight % of ethylcellulose, 22.86 weight % of titanium oxide, and 8.57 weight % of diethylphthalate.

15. The method of claim 14, wherein the coating solution is an aqueous solution obtained by dissolving polyvinyl alcohol as the oil-proof material and polyethylene glycol (PEG) as a plasticizer.

* * * * *